United States Patent [19]

Sohde et al.

[11] 4,097,234

[45] Jun. 27, 1978

[54] METHOD FOR PREPARING DISPERSION OF COLLAGEN FIBER

[75] Inventors: Takeshi Sohde, Chiba; Astuko Gotoh, Ichikawa; Kuniharu Iwamoto, Sohka; Yasushi Okamoto, Ichikawa, all of Japan

[73] Assignee: Nippi, Incorporated, Tokyo, Japan

[21] Appl. No.: 749,307

[22] Filed: Dec. 10, 1976

[51] Int. Cl.² .............................................. C14C 3/00
[52] U.S. Cl. ................................... 8/94.19; 8/94.26; 8/94.27; 8/94.28; 8/94.29; 8/94.33; 260/123.7
[58] Field of Search ............. 8/94.19 R, 94.26, 94.27, 8/94.28, 94.29, 94.33; 260/123.7

[56] References Cited

U.S. PATENT DOCUMENTS

| 3,637,642 | 1/1972 | Fuji | 260/118 |
|---|---|---|---|
| 3,894,132 | 7/1975 | Daniel | 8/94.11 |
| 4,021,522 | 5/1977 | Daniel | 8/94.11 |

FOREIGN PATENT DOCUMENTS 7,115,033   4/1971   Japan.

*Primary Examiner*—A. Lionel Clingman
*Attorney, Agent, or Firm*—Hans Berman

[57] ABSTRACT

A method for preparing an aqueous dispersion of collagen fibers from various materials containing insoluble collagen and various products prepared from the dispersion are disclosed.

9 Claims, No Drawings

METHOD FOR PREPARING DISPERSION OF COLLAGEN FIBER

This invention relates to a method for preparing a dispersion of collagen fibers from various materials containing insoluble collagen and also relates to various products prepared from the dispersions. More particularly, this invention relates to a method for preparing an aqueous dispersion of collagen fibers which comprises the following procedures: the starting material such as hides skins, tendons etc., of an animal which consists mostly of insoluble collagen is treated with an aqueous solution containing sodium hydroxide, sodium sulfate and a small amount of an amine or a basic organic compound; this treatment loosens the network structures of the starting material and, as a consequence, the structures can be crushed easily and, further, the treatment decomposes the telopeptides, which are located at both ends of the tropocollagen molecules and loosens the fiber-bundles of collagen having the structure of reticulin but keeps intact the native type structures of higher orders of collagen fiber. The dispersion of the fiber-bundles of collagen is treated with a collagen tanning agent, the pH range is adjusted to 2.0–4.0 or 9.0–11.0, and crushed mechanically to give a dispersion comprised only of collagen fibers.

The collagen molecule (tropocollagen) consisting of three polypeptide helices is a rigid rod with a diameter of 14 Å and a length of 3000 Å; in both end-regions the component peptides constitute non-helical portions, which are called telopeptides, and these are of great importance in the formation of native type fibrils. Collagen protein is inherently low in antigenicity and further the most of its antigenicity are assumed to result from the telopeptide regions. This assumption is supported by the fact that the tropocollagen of which the telopeptide regions have been digested are extremely low in antigenicity.

Collagen exists in vivo primarily in the form of fibrils which compose the special packing arrangement of tropocollagen molecules, i.e., an arrangement in which neighboring tropocollagen molecules or linear aggregates thereof (protofibrils) are displaced longitudinally with respect to one another by a distance equal to ¼ of the length of the component molecules. The fibrils exhibit, by electron microscopy, marked stripes, the distance between which is about 640 Å (690 Å in the wet state). While the diameter of the fibrils depends on the sort of collagen sources such as the animal species and the kind of tissue, it is in the range 1000 – 2000 Å in the dry state for the collagen of the mature cattle hide.

The next higher order unit of the parallel packing arrangement of fibrils is called the fiber of collagen and its diameter in the dry state is in the range 2 – 6 $\mu$ for the mature cattle hide. Being packed into a bundle, the fibers give a collagen fiber-bundle having a diameter of 20 – 100 $\mu$ in the dry state, the surface of which is covered with the thin layer of reticulin. Collagen exists mostly in the fiber-bundle state in the native tissues, where the fiber-bundles constitute the network structure which gives the characteristic persistence and pliability to the tissues.

Collagen is the major protein in connective tissues of animals, such as the hide, the tendon, the bone, the cornea etc. and occurs there mostly in the form of collagen fiber-bundles or fibers. In general, the diameter of collagen fiber-bundles depends on the sort of the tissue as well as the age of the animal as the collagen source.

For example, the diameter of the fiber-bundles of calf skin in the dry state is in the range of 20 – 30 $\mu$ and the component fibers are not firmly tied up in this case, while the fiber-bundles of the mature cattle hide have a diameter in the range of 40 – 100 $\mu$ and the reticulin layer which gives stability to the fiber-bundles by covering each of them is so firm in this case that the fibers which compose a fiber-bundle are not able to be separated into independent fibers. The length of the fiber-bundle in this case is longer than that for the calf skin and its maximum value amounts to several tens of centimeters. The fiber-bundles, together with elastin, mucoprotein and other components, constitute the corium layer.

The dispersions of collagen fiber which have been applied so far for the various uses were prepared in the following way. Hides or tendons were washed, swollen in an acid or alkaline medium and crushed. However, when the pH of hides or tendons is in the range where the collagen is to be solubilized or is easy to swell, if the hides or tendons are violently stirred or crushed mechanically, the collagen fibers are degraded or torn into smaller pieces and give collagen fibrils, collagen molecules, or the intermediates between the fibril and the molecule. The dispersions obtained in this way are too highly viscous to be treated effectively and tend to be denatured owing to the heat of friction during the mechanical stirring or crushing of them. Further, the length of the fibers and fibrils contained in the dispersions lacks uniformity and most are too short and the products (for example, films) prepared from the dispersion are unsatisfactory with respect to mechanical properties, especially tear strength.

The present inventors have overcome the foregoing problems and disadvantages and have succeeded in the production of collagen dispersion which manifest low enough viscosity and contain only exclusively collagen fibers of controllable fiber lengths without collagen fibrils, tropocollagens and the intermediates between the fibril and the tropocollagen. Further, it has now been discovered that such products as non-woven fabrics, cotton, films, spun fibers etc. which have many excellent properties can be prepared from the dispersions of the collagen fibers of longer fiber-lengths.

Although the animal tissues are treated by a procedure analogous to that described in Japanese Patent Publication 15033/71, the present invention differs from invention of the Publication, because in this invention the insoluble collagen is not solubilized but its native fiber structures are left intact in order to make use of their characteristic properties which should be exhibited in the end products.

Such starting materials as hide, tendon and others are washed with water and an aqueous salt solution and then soaked in an aqueous solution consisting of (a) 0.3 – 1.0 N of sodium hydroxide, (b) 10 – 20% (w/w) of sodium sulfate, and (c) 0.05 – 0.3 mol of a basic organic compound at a temperature between 15° and 25° C for a period of 5 hrs. to 10 days, preferably for 1 to 7 days, wherein the basic organic compound used may be selected from hydrazine, hydroxylamine and the primary and secondary alkyl amines which contain 1 to 5 carbon atoms in each molecule of a normal chain, branched chains or a ring, and to which belong, for example, monomethylamine, dimethylamine, monoethylamine, diethylamine, ethylendiamine, piperidine, piperazine, etc.

The content of the telopeptides in collagen which are situated in the end regions of collagen molecules can be controlled depending upon the duration of the alkali treatment. Since tyrosine is situated only in the telopeptide regions of collagen, the tyrosine content of collagen is proportional to that of the telopeptide. The telopeptide contents expressed in terms of the tyrosine contents are shown in the following table as a function of the periods of the alkali treatment.

| Duration of the alkali treatment (days) | 0 | 1 | 3 | 7 | 21 |
|---|---|---|---|---|---|
| Tyrosine content (residues/1000 residues) | 3.5 | 2.6 | 1.6 | 0.84 | 0.47 |

It is a remarkable feature of this invention that the products for medical uses produced with the collagen fiber can be made to be very low in antigenicity by extending the duration of the alkali treatment of the insoluble collagen within the limit indicated above and promoting the decomposition of telopeptides.

The alkali treated collagen is washed with water for desalting, its pH may be then adjusted to a pH between 3.5 and 9.5, if necessary, and finally the collagen fiber-bundle is obtained by crushing the resultant collagen mechanically, for example, by the use of a mincer and either a homogenizer (a dispersing mill or a refiner) or a roller. The length of the collagen fiber-bundle obtained depends on the size of holes in the plate of the mincer and is preferably in the range between 5 to 70 mm. In order to obtain this length, a mincer with a hole size in the range between 2 to 50 mm in diameter may be used.

The collagen fiber-bundle obtained must be tanned with a conventional tanning agent for collagen, which includes aldehydes such as formaldehyde, acetoaldehyde, glyoxal, glutaraldehyde etc., metallic salts such as chromium complex salts, aluminium sulfate, ferric sulfate, etc. or a natural tanning agent such as a smoke liquid. The sort and quantity of the tanning agent to be used should be determined depending upon the use of the end product — medical, edible, daily or industrial use. It is preferable to tan in the presence of an adequate amount of a neutral salt in any case. In the case of the aldehyde tannage the pH of the reaction mixtures is in the range of 4 to 10 and the concentration of aldehyde in the aqueous reaction mixtures is in the range of 0.005 to 2.0%. For the metallic salt tannage the pH of the reaction mixtures is in the range of 2.5 to 5.0, and the concentration of the reagent metallic salts in the aqueous solutions is in the range of 0.3 to 1.0% for the chromium complex salt "Hi-Neochrome ®" (manufactured by Nippon Kagaku Kogyo K.K. and containing 30% chromium converted to $Cr_2O_3$ basis), in the range of 1.0 to 10% $Al_2(SO_4)_3$ for aluminium sulfate tannage, or in the range of 0.5 to 5% $Fe_2(SO_4)_3$ for ferric sulfate tannage. In the case of the smoke liquid tannage the pH of the reaction mixtures is in the range of 4 to 10, and the total concentration of aldehydes in the aqueous solutions is in the range of 0.01 to 1.0% converted to a formaldehyde basis. In the above mentioned tanning treatments the temperature and time of reaction are adjusted generally to be in the range of 25° to 35° C and 2 to 40 hours, respectively, and the tanned products are washed with running water for about 2 hours.

The collagen fiber-bundle tanned with a tanning agent of collagen is crushed and homogenized mechanically by a homogenizer (e.g., a dispersing mill or a refiner) after the pH has been adjusted to either between 2.0 and 4.0 or between 9.0 and 11.0. Thus the collagen fiber dispersion is obtained. The diameter of the collagen fibers is usually in the range of 4 – 12 $\mu$ and the length is usually in the range of 2 – 25 mm. The distance between both edges in the dispersing mill or the refiner used in this case is narrower than that used for the production of the fiber-bundle. The collagen fiber dispersion may be shaped into various forms, for example, non-woven fabric or cotton, films to be used for covering meat, sea foods, fruits, vegetables and other perishables; bag-shaped collagen membranes such as the fingerstall, the gloves, the condom etc.; tubes such as are used for sausage casing or the artificial kidney membrane; tubes or sheets to be sewn such as artificial blood vessels, artificial esophagus, artificial dura, artificial tympanum, membranes for preventing adhesion, artificial cornea etc. Other collagen membranes are used for medical, edible, daily, and industrial purposes. It is shaped also into surgical sutures and strings for use in tennis, etc. The collagen wool produced from the resultant fiber dispersion is comprised of homogeneous fibers which retain their softness after dehydration and drying by means of lyophilization or by the use of alcohols such as ethanol, methanol etc. These products can be used as first-aid adhesive plaster, hemostatic, etc. The resultant fiber dispersion membranes formed are able to be sewn even in a wet state, when the membrane has been cast and airdried to thickness in the range of 50 to 200 $\mu$, preferably in the range of 70 to 100 $\mu$. If desired, the membranes obtained in this way may be tanned once again. Further, after having been mixed with the molecularly solubilized collagen solutions and/or insoluble collagen dispersions prepared by a usual method and having been shaped by an established method, the collagen fiber dispersion may be converted into membranous collagen products in the form of a bag, tube, sheet or filliform products such as surgical sutures, the guts of rackets for tennis and badminton etc. which have outstanding mechanical properties.

EXAMPLE

The butt portions of steer hides, immediately after slaughter or salt-curing, were dehaired and washed with water. The grain and flesh-side layers were cut off and washed with water. The corium of the hides obtained was cut into 10 cm square sections, which were washed first with a 10% solution of sodium chloride and then thoroughly with water. The corium so obtained contained 25% (w/w) insoluble collagen. This corium (400 g) was soaked in 600 ml of an aqueous solution containing 20 g sodium hydroxide, 160 g sodium sulfate and 20.7 g of a 30% monomethylamine aqueous solution for 7 days at 20° C, and washed with water for desalting. The pH of the resultant corium was then adjusted to 6.0 with hydrochloric acid. After being held for 24 hours, the corium was ground first by the use of a mincer with a hole diameter of 7 mm and then completely by employing a dispersing mill. The ground product thus obtained and consisting mostly of fiber-bundle (100 g by dry weight) was dispersed into 10 l. of a 15% (w/v) solution of sodium sulfate and adjusted to a pH of 8.5 with 2N sodium carbonate solution. To this slurry was added 200 ml. of a 25% glutaraldehyde solution and the tanning process proceeded for 5 hours at 25° C. After the tanning step, the dispersion was washed with water, adjusted to a volume of 5 l. with water (where the concentration of the collagen substance is 2.0%), and then adjusted to a pH of 3.0 with 2N hydrochloric acid. The slurry so obtained was ground by the use of a dispersing mill. Microscopy indicated that the collagen dispersion finally obtained consisted mostly of collagen fibers and contained almost neither fiber-bundles nor fibrils, that the diameter of the collagen fibers was in the range of 4 – 12 $\mu$ and that the length of the collagen fibers had not been decreased distinguishably from that of the fiber-bundles at the start and was in the range of 2 – 25 mm. The final slurry prepared as described in this Example had a viscosity value amounting to 1/5 – 1/20 that of collagen dispersion products obtained by following a prior art procedure.

What is claimed is:

1. A method of preparing an aqueous dispersion of collagen fibers which comprises:
   (a) soaking a material including bundles of collagen fibers in an aqueous solution 0.3 to 1.0 normal with respect to NaOH, and containing 10% to 20% $Na_2SO_4$ by weight and 0.05 to 0.3 mole per liter of an organic base until a portion of the telpeptides is removed from the collagen molecules in said bundles,
      (1) said bundles having a length greater than 5 mm when being soaked in said solution,
      (2) a length of said bundles greater than 5 mm being maintained during said soaking;
   (b) washing the soaked material with water;
   (c) grinding the washed material until said fiber bundles have a length of 5 to 70 mm;
   (d) tanning the ground fiber bundles; and
   (e) comminuting the tanned fiber bundles in an aqueous medium at a pH of 2.0 – 4.0 or 9.0 to 11.0 until an aqueous dispersion of collagen fibers having a length of at least 2 mm is formed.

2. A method according to claim 1 wherein said soaking is carried out at a temperature of 0° – 37° C for 1 – 7 days.

3. A method according to claim 2 wherein said temperature ranges from 25° – 35° C.

4. A method according to claim 1 wherein said organic base is a primary or secondary amine having 1 – 5 carbon atoms, hydrazine or hydroxylamine.

5. A method according to claim 1 wherein said organic base is selected from the group consisting of hydroxylamine, monomethylamine and dimethylamine.

6. A method according to claim 1 wherein said grinding step is carried out by the sequential use of a mincer and a homogenizer.

7. A method as set forth in claim 1, wherein said ground fiber bundles are tanned by means of a tanning agent selected from the group consisting of formaldehyde, acetaldehyde, glyoxal, glutaraldehyde, chromium complex salt, aluminum sulfate, ferric sulfate, and smoke liquid.

8. A method as set forth in claim 1, wherein said tanned fiber bundles are comminuted in a dispersing mill.

9. A method as set forth in claim 1, wherein said tanned fiber bundles are comminuted until the collagen fibers in said dispersion have a diameter of 4 to 12 $\mu$ and a length of 2 to 25 mm.

* * * * *